US011414465B2

(12) United States Patent
Yu et al.

(10) Patent No.: US 11,414,465 B2
(45) Date of Patent: Aug. 16, 2022

(54) **PLASMA MEMBRANE INTRINSIC AQUAPORIN FOR ABSORBING AND TRANSPORTING NEONICOTINOID INSECTICID

(56) References Cited

OTHER PUBLICATIONS

Chen Y, Sun S K, Tang Z, et al. The Nodulin 26-like intrinsic membrane protein OsNIP3;2 is involved in arsenite uptake by lateral roots in rice Journal of Experimental Botany, 2017, 68(11):3007-3016.

Sun S K, Chen Y, Che J, et al. Decreasing arsenic accumulation in rice by overexpressing OsNIP1;1 and OsNIP3;1 through disrupting arsenite radial transport in roots. New Phytologist, 2018.

Moller I M. Plant mitochondria and oxidative stress: electron transport, NADPH turnover, and metabolism of reactive oxygen species. Annual Review of Plant Biology, 2001, 52(4):561-591.

Liu T, et al. Unconventionally secreted effectors of two filamentous pathogens target plant salicylate biosynthesis. Nat Commun 5, 4686. 2014.

Wenfeng W, Wan Q, Li Y, et al. Uptake, translocation and subcellular distribution of pesticides in Chinese cabbage (*Brassica rapa* var. chinensis)[J]. Ecotoxicology and Environmental Safety, 2019.

He Lin, Jiang Lili, Wang Yucheng, Analysis of the stress tolerance of Tamarix thioredoxin peroxidase (ThPrx1) gene transformed into yeast, Journal of Northeast Forestry University, 2011, vol. 39 No.4, 101-104.

Valvekens, D., van Montagu, M., and Lijsebettens, M. V. (1988). Agrobacterium tumefaciens-mediated transformation of *Arabidopsis thaliana* root explants by using kanamycin selection. Proc. Natl. Acad. Sci. USA 85, 5536-5540.

\* cited by examiner

Thiamethoxam

Imidacloprid

Acetamiprid

Nitenpyram

Dinotefuran

Nicotine

PLASMA MEMBRANE INTRINSIC AQUAPORIN FOR ABSORBING AND TRANSPORTING NEONICOTINOID INSECTICIDES, AND CODING GENE AND USE THEREFOR

CROSS-REFERENCE TO RELATED APPLICATIONS

The present application claims the priority of Chinese Patent Application No. 202010386724.X, filed on May 9, 2020 and entitled by "SEMICONDUCTOR DEVICE AND MANUFACTURING METHOD THEREOF", which is incorporated herein by reference in its entirety.

A sequence listing in the ASCII text file with a ".txt" extension via EFS-Web is herein incorporated by reference. Said sequence listing in the ASCII text file with a ".txt" extension is named "21217YWX_ST25", date of creation is Sep. 10, 2021, size is 5 KB.

TECHNICAL FIELD

The disclosure belongs to the technical field of biology, and in particular relates to a plasma membrane intrinsic aquaporin derived from Chinese cabbage and application thereof in improving the transport and utilization efficiency of crop neonicotinoid insecticides.

BACKGROUND ART

Neonicotinoid insecticides (such as thiamethoxam, imidacloprid, acetamiprid, nitenpyram and dinotefuran) have become the fastest growing insecticides in the global market, accounting for 24% of the insecticide market and 80% of the seed coating agent market. Neonicotinoid insecticides are synthetic compounds similar to the natural insecticide nicotine in structure, and target nicotinic acetylcholine receptors (nAChRs) in the central nervous system of insects. That is, nitrogen atoms in an imidazolidine ring interact with amino acid residues of the insect nAChRs, blocking the receptors and causing the insects to paralyze and die. Such mechanism makes the neonicotinoid insecticides more selective and less toxic to non-target organisms than traditional insecticides. Thiamethoxam is an efficient, safe, highly selective, and low-toxic second-generation neonicotinoid insecticide developed by Novartis of Switzerland in 1991, and contains a chlorothiazole ring which increases the broad-spectrum effect and improves activity. Thiamethoxam has high polarity, high solubility, and strong systemic action, and is used for stem and leaf spray, soil irrigation and seed treatment. After application, thiamethoxam is transported by leaves or roots quickly to all parts of the plant through systemic action, and can effectively control aphids, leaf miners and other pests.

Aquaporins mainly promote two-way transmembrane movement of water. Aquaporin-mediated free water is rapidly and passively transported across a biomembrane, and is the main way for water to enter and exit cells. The first plant aquaporin γ-TIP was isolated from *Arabidopsis thaliana* in 1993 by Maurel et al. (Maurel C, Reizer J, Schroeder J I, et al. The vacuolar membrane protein gamma-TIP creates water specific channels in *Xenopus oocytes*. The EMBO Journal, 1993, 12(6):2241-2247.). Plant aquaporins are all members of the MIP superfamily. Aquaporins in different plants have highly homologous molecular structures and very conserved sequences. In terms of molecular structure, there are typical 6 transmembrane domains and 5 rings, which are named A, B, C, D and E rings, respectively. All members contain a very highly conserved NPA structure (Asn-Pro-Ala, NPA) in the B ring and the E ring. Johanson et al. (Johanson U. The complete set of genes encoding major intrinsic proteins in *Arabidopsis* provides a framework for a new nomenclature for major intrinsic proteins in plants. Plant Physiology, 2001, 126(4):1358-69.) divide aquaporins, according to amino acid sequence homology and subcellular localization, into 5 families: plasma membrane intrinsic proteins (PIPs), tonoplast intrinsic proteins (TIPs), Nodulin 26-like intrinsic proteins (NIPs), small basic intrinsic proteins (SIPs) and GlpF-like intrinsic proteins (GIPs). In addition to the 5 types of aquaporins above, Sphaerotheciella also contains 2 new types of XIPs and HIPs. (Bienert G P, Bienert M D, Jahn T P, et al. Solanaceae XIPs are plasma membrane aquaporins that facilitate the transport of many uncharged substrates. Plant Journal, 2011, 66(2):306-317.).

In addition to transporting water molecules, studies have found that aquaporins can also transport some small molecules such as glycerol, silicic acid, ammonium, urea, boric acid, $CO_2$, arsenite, $H_2O_2$, and ammonia. Studies of Bienert et al. (2011) showed that Solanaceae XIPs can promote the transport of some neutral small molecules such as glycerol and urea. Silicon can improve the root water uptake and increase the activity of aquaporins (Liu P, Yin L, Deng X, et al. Aquaporin-mediated increase in root hydraulic conductance is involved in silicon-induced improved root water uptake under osmotic stress in *Sorghum bicolor* L. Journal of Experimental Botany, 2014, 65(17):4747-4756.). In *Arabidopsis thaliana*, AtNIP6;1 and AtNIP7;1 are involved in the transport of boron and can adjust the nutrient distribution ratio of boron in the aboveground part and pollen (Li T, Choi W G, Wallace I S, et al. *Arabidopsis thaliana* NIP7;1: an anther-specific boric acid transporter of the aquaporin superfamily regulated by an unusual tyrosine in helix 2 of the transport pore. Biochemistry, 2011, 50(31): 6633-6641.). Terashima et al. (Terashima I, Ono K. Effects of $HgCl_2$ on $CO_2$ dependence of leaf photosynthesis: evidence indicating involvement of aquaporins in $CO_2$ diffusion across the plasma membrane. Plant Cell Physiology, 2002, 43(1): 70-78.) proved that aquaporins can promote the transport of $CO_2$ on the plasma membrane and improve photosynthesis of plants by using $HgCl_2$ inhibitors. A functional expression experiment of yeast cells and *Xenopus oocytes* showed that ZmPIP1;5 and ZmPIP1;6 can improve the transport of $CO_2$ in *Arabidopsis thaliana* guard cells (Heinen R B, Bienert G P, Cohen D, et al. Expression and characterization of plasma membrane aquaporins in stomatal complexes of *Zea mays*. Plant Molecular Biology, 2014, 86(3):335-350.). Rice OsNIP2;1, OsNIP1;1 and OsNIP3;3 are involved in arsenite uptake in rice, and OsNIP3:2 is involved in trivalent arsenic uptake in rice (Chen Y, Sun S K, Tang Z, et al. The Nodulin 26-like intrinsic membrane protein OsNIP3;2 is involved in arsenite uptake by lateral roots in rice. Journal of Experimental Botany, 2017, 68(11):3007-3016.; Sun S K, Chen Y, Che J, et al. Decreasing arsenic accumulation in rice by overexpressing OsNIP1;1 and OsNIP3;1 through disrupting arsenite radial transport in roots. New Phytologist, 2018.). Studies of Moller et al. (Moller I M. Plant mitochondria and oxidative stress: electron transport, NADPH turnover, and metabolism of reactive oxygen species. Annual Review of Plant Biology, 2001, 52(4):561-591.) showed that AQP8 can promote the release of $H_2O_2$ from the mitochondrial matrix. The reports above involve a number of small molecules with large differences in structure, but larger molecules (such as a neonicotinoid insecticide thiamethoxam) have not yet been reported related to aquaporins. Also, there is no report on the transport of neonicotinoid insecticides by aquaporins.

SUMMARY OF THE INVENTION

In view of the problems above, the disclosure is directed to provide a new plasma membrane intrinsic aquaporin responsible for transmembrane transport of neonicotinoid insecticides and an encoding gene thereof. The gene is a DNA molecule isolated from Chinese cabbage, named BraPIP1;1 by the applicant. The disclosure also provides application of the plasma membrane intrinsic aquaporin in improving the transport efficiency of plant neonicotinoid insecticide thiamethoxam.

Specifically, the disclosure is implemented through the following technical solutions:

First, an embodiment of the disclosure provides a plasma membrane intrinsic aquaporin, having an amino acid sequence as set forth in SEQ ID NO. 2. The plasma membrane intrinsic aquaporin is derived from Chinese cabbage and is located on the plasma membrane. Through a molecular docking technology, it is found that neonicotinoid insecticide molecules can pass through pores of the protein. Compared with an environment with no neonicotinoid insecticide (thiamethoxam) added, the plasma membrane intrinsic aquaporin has a significantly enhanced expression abundance in an environment with thiamethoxam added, and has the characteristics of powerfully mediating the transmembrane transport of thiamethoxam. Also, after an aquaporin inhibitor is added, the uptake of different neonicotinoid insecticides in Chinese cabbage can be inhibited.

Second, an embodiment of the disclosure provides an encoding gene BraPIP1;1 of a plasma membrane intrinsic aquaporin having an amino acid sequence as set forth in SEQ ID NO. 2, and the nucleotide encoding sequence of the encoding gene is as set forth in SEQ ID NO.1. A method for cloning the gene is as follows: the total RNA is extracted from the roots of Chinese cabbage by using an RNA simple Total RNA Kit (Tiangen Biotech, Beijing, China); according to the steps of a Primescript 1st Strand cDNA Synthesis Kit (Invitrogen), 2 g of total RNA is used as a template and oligo (dT)18 is used as an anchor primer to synthesize 1st strand cDNA; according to the amino acid sequence information of PIP1;1 in the transcriptome analysis results of Chinese cabbage in our laboratory, a degenerate primer for a conserved region is designed; using the 1st strand cDNA synthesized above as a template, an ORF sequence is amplified by the degenerate full-length primer; and the amplified PCR product is sent for sequencing, and named BraPIP1;1 by the applicant.

Third, an embodiment of the disclosure provides a recombinant expression vector containing the encoding gene BraPIP1;1. Further, the recombinant expression vector is a *Saccharomyces cerevisiae* expression vector, and the *Saccharomyces cerevisiae* expression vector includes but is not limited to the vector pYES2.

Fourth, an embodiment of the disclosure provides a binary overexpression vector containing the encoding gene BraPIP1;1, and the binary overexpression vector includes but is not limited to the vector pCAMBIA2301.

Fifth, an embodiment of the disclosure provides application of the plasma membrane intrinsic aquaporin, having an amino acid sequence as set forth in SEQ ID NO. 2, in improving the uptake and transport efficiency of neonicotinoid insecticides in plants. The plants include at least one of vegetables (Chinese cabbage, etc.), rice, *Zea mays*, wheat, rape, and *Arabidopsis thaliana*; and the neonicotinoid insecticides include one or more of thiamethoxam, imidacloprid, acetamiprid, nitenpyram, and dinotefuran.

Sixth, an embodiment of the disclosure discloses a method for promoting the uptake and transport of neonicotinoid insecticides in plants, including: introducing a binary overexpression vector containing a nucleotide sequence as set forth in SEQ ID No. 1 into plants for expression, thereby promoting the uptake and transport of the neonicotinoid insecticides in the plants. The binary overexpression vector includes but is not limited to the vector pCAMBIA2301; the plants are preferably at least one of vegetables, rice, *Zea mays*, wheat, rape, and *Arabidopsis thaliana*; and the neonicotinoid insecticides are preferably at least one of thiamethoxam, imidacloprid, acetamiprid, nitenpyram, and dinotefuran.

The disclosure found for the first time that aquaporins are involved in the transmembrane transport of neonicotinoid insecticides, also found for the first time the BraPIP1;1 gene resource in the plasma membrane intrinsic aquaporin and identified the functions thereof. The Chinese cabbage plasma membrane intrinsic aquaporin provided by the disclosure is mainly located in the plasma membrane, can mediate the transport of neonicotinoid molecules, and has the characteristic of sensitively responding to thiamethoxam in the external environment. At the same time, it has the function of rapidly mediating thiamethoxam across the cell membrane, promoting the accumulation of thiamethoxam in plants, which has important application value in the development of pesticides.

BRIEF DESCRIPTION OF THE DRAWINGS

FIG. 1 is a schematic diagram of subcellular localization of the BraPIP1;1 protein;

tobacco leaf cells instantaneously transformed for 48 hours under confocal microscope observation. Scale=40 μm.

FIG. 2 shows the effect of water channel inhibitors on the uptake of different neonicotinoid insecticides and nicotine in Chinese cabbage (FIG. 2A: thiamethoxam; FIG. 2B: imidacloprid; FIG. 2C: acetamiprid; FIG. 2D: nitenpyram; FIG. 2E: dinotefuran; and FIG. 2F: nicotine).

FIG. 3 shows the molecular docking analysis of BraPIP1;1 with different neonicotinoid insecticides and nicotine.

FIG. 4 is a schematic diagram of the expression characteristics of BraPIP1;1 and response characteristics thereof to thiamethoxam, where FIG. 4A shows the response characteristics of the root tissue BraPIP1;1 to external thiamethoxam; and FIG. 4B shows the response characteristics of the aboveground tissue BraPIP1;1 to external thiamethoxam.

FIG. 5 is a schematic diagram of the growth and the thiamethoxam content of a BraPIP1;1 recombinant yeast strain under thiamethoxam stress, where FIG. 5A shows the growth of the recombinant yeast under different concentrations of thiamethoxam; and FIG. 5B is a schematic diagram of the thiamethoxam content in the recombinant yeast strain.

FIG. 6 is a schematic diagram of the growth and the thiamethoxam content of BraPIP1;1 transgenic *Arabidopsis thaliana* plants under thiamethoxam stress, where FIG. 6A shows the growth of the transgenic *Arabidopsis thaliana* plants under different concentrations of thiamethoxam; FIG. 6B is a schematic diagram of the main root length of the transgenic *Arabidopsis thaliana* plants under different concentrations of thiamethoxam; FIG. 6C is a schematic diagram of the thiamethoxam content of the transgenic *Arabidopsis thaliana* plants; and BraPIP1;1#4 and BraPIP1;1#6 are overexpression *Arabidopsis thaliana* lines.

DETAILED DESCRIPTION OF THE INVENTION

The technical solutions of the disclosure will be further described below in conjunction with examples.

EXAMPLE 1

Cloning and Analysis of the Full-Length Encoding Region of BraPIP1;1 Gene

1. ORF Amplification of BraPIP1;1

The total RNA was extracted from a root sample of Chinese cabbage according to operation steps of using an RNA simple Total RNA Kit (Tiangen Biotech, Beijing, China). Using 2 g of total RNA as a template and oligo (dT)18 as an anchor primer, and referring to instructions of a Primescript 1st Strand cDNA Synthesis Kit (Invirtrogen), 1st strand cDNA was synthesized. Primers were designed to perform PCR amplification to obtain a single cDNA fragment, and the primer sequences are as follows: upstream primer sequence (SEQ ID NO.3): ATG-GAAGGCAAGGAAGAAGACG; and downstream primer sequence (SEQ ID NO.4): TTAGTTTCTGGACTT-GAAGG.

An amplification system is 50.0 μL in total volume, including 20 ng of cDNA, 10.0 μL of 5×Prime STAR buffer, 4.0 μL of 2.5 mmol·L$^{-1}$ dNTPs, 2.0 μL of 10 mmol·L$^{-1}$ forward primer and reverse primer each, 1.25 U of Prime-STAR HS DNA Polymerase, and the balance of redistilled water.

An amplification program is: pre-denaturation at 95° C. for 5 min, denaturation at 98° C. for 10 s, renaturation at 55° C. for 15 s, and extension at 72° C. for 60 s, 35 cycles in total.

The PCR product was sent to Tsingke Biotechnology Co., Ltd. for sequencing. The sequencing result shows that the full-length cDNA sequence of BraPIP1;1 is 2550 bp. The cDNA of BraPIP1;1 and the amino acid sequence of a protein encoded by BraPIP1;1 are as set forth in SEQ ID No. 1 and SEQ ID No. 2, respectively.

EXAMPLE 2

Subcellular Localization of BraPIP1;1

Figure 1:
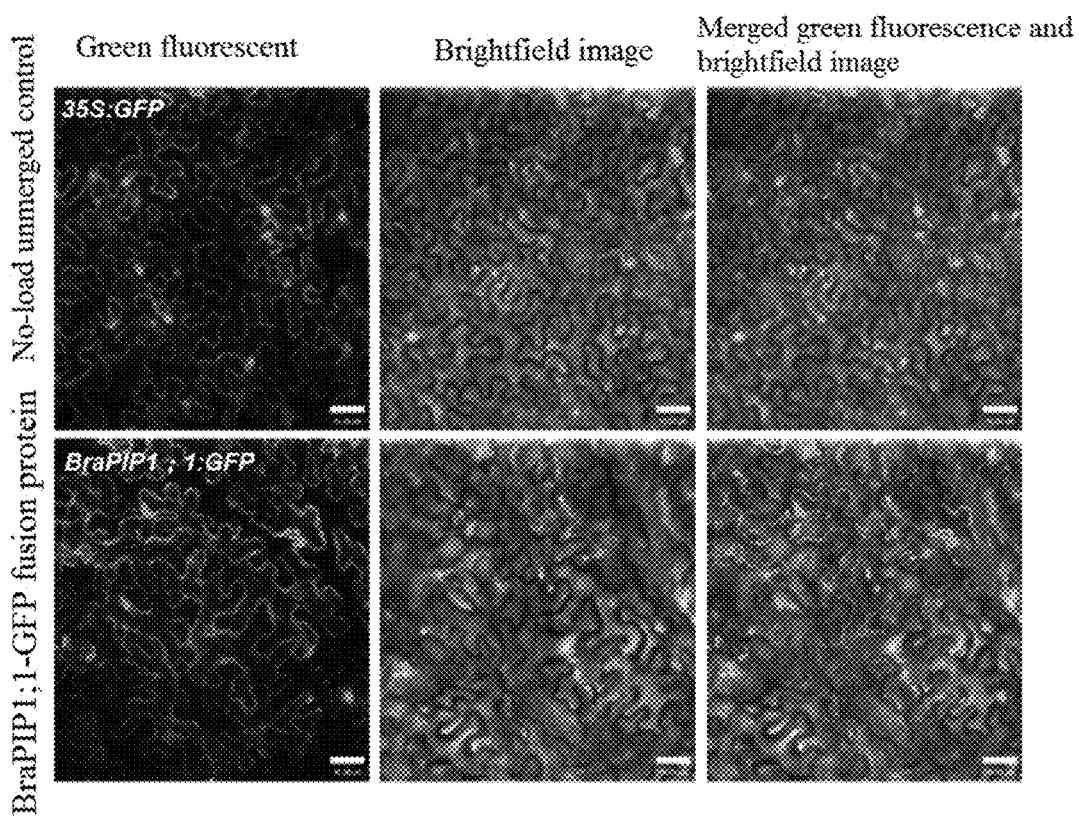

Referring to Liu et al. (Liu T, et al. Unconventionally secreted effectors of two filamentous pathogens target plant salicylate biosynthesis. Nat Commun 5, 4686. 2014), BraPIP1;1 was constructed into a subcellular localization vector pBinGFP4, and transformed into an *Agrobacterium* strain GV3101 (deposited in the laboratory of Jiangsu Academy of Agricultural Sciences in the present example, and other commercially available products may also be used in specific applications) by a freeze-thaw method. Tobacco was transformed instantaneously, and fluorescence was observed under a fluorescence microscope after 48 h-60 h. It was found that the green fluorescent signal was mainly distributed on the cell membrane or nuclear membrane (see FIG. 1), indicating that BraPIP1;1 is mainly located on the cell membrane and nuclear membrane related to transmembrane transport.

EXAMPLE 3

Inhibiting the Activity of Aquaporins Can Reduce the Uptake and Accumulation of Neonicotinoid Pesticides in Vegetables Referring to the paper (Wenfeng W, Wan Q, Li Y, et al. Uptake, translocation and subcellular distribution of pesticides in Chinese cabbage (*Brassica rapa* var. *chinensis*)[J]. Ecotoxicology and Environmental Safety, 2019.), water channel inhibitors, mercuric chloride and glycerol, of different concentrations were added to equal volumes of Hoagland nutrient solutions containing 2 mg/L nicotine compounds (thiamethoxam, imidacloprid, acetamiprid, nitenpyram, dinotefuran and nicotine). After 48 h, the concentrations of the nicotine compounds in the Chinese cabbage plants (with three leaves and one bud) were determined respectively. Each treatment was repeated five times.

To determine whether aquaporins can transport the neonicotinoid insecticide molecules and nicotine, the water channel inhibitors mercuric chloride (HgCl$_2$) and glycerol of different concentrations were added to equal volumes of nutrient solutions containing 2 mg/L of different neonicotinoid insecticides (thiamethoxam, imidacloprid, acetamiprid, nitenpyram and dinotefuran) and nicotine, and the concentrations of the nicotine compounds in the plants were determined respectively.

Figure 2:
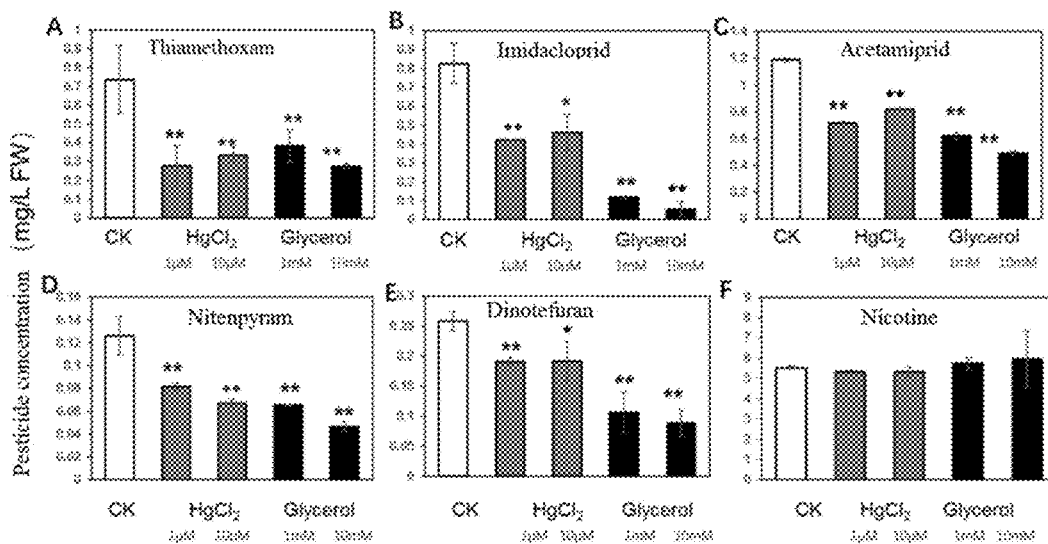

The test results are as shown in FIG. 2. After the water channel inhibitors were added, the content of the neonicotinoids in the plants was significantly reduced, while the content of nicotine in the plants did not change significantly. It can be seen that, the water channel inhibitors can significantly inhibit the uptake of the neonicotinoid insecticides in Chinese cabbage, but not the uptake of nicotine, indicating that the aquaporins are involved in the transmembrane transport of the neonicotinoid insecticides.

EXAMPLE 4

Molecular Docking Analysis of BraPIP1;1 Protein with Different Neonicotinoids and Nicotine A 3D structure of BraPIP1;1 was obtained by homology modeling of the BraPIP1;1 amino acid sequence, and whether the neonicotinoid insecticide molecules (thiamethoxam, imidacloprid, acetamiprid, nitenpyram and dinotefuran) and nicotine molecules can pass through the pores in the middle of the BaPIP1;1 crystal structure was verified with the molecular docking technology. The docking range includes the whole protein conformation, so the docking results of the neonicotinoid insecticide molecules and nicotine molecules entering the central pores of the protein can be screened from many conformations generated to analyze whether the insecticide-like molecules can pass through the protein pores.

Figure 3:
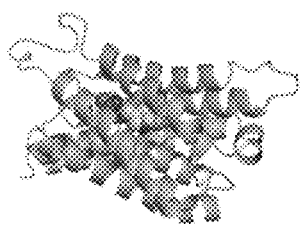
Figure 3:
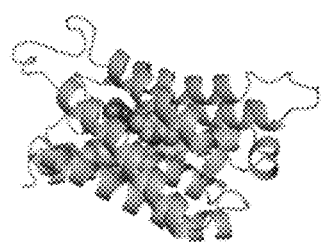
Figure 3:
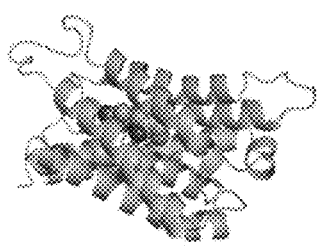
Figure 3:
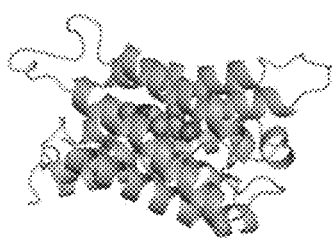
Figure 3:
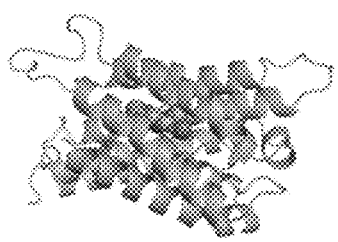
Figure 3:
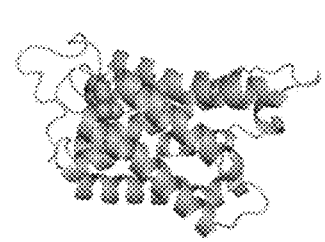

The software used for docking is AutoDockTools-1.5.6, the size of a docking box is set to 100 Å*126 Å*100 Å, semi-flexible docking is adopted, the algorithm uses the Lamarckian genetic algorithm, and the docking generates 200 results. The docking result is shown in FIG. 3: The neonicotinoid insecticide molecules (thiamethoxam, imidacloprid, acetamiprid, nitenpyram and dinotefuran) bind to the center of the protein channel, which proves that thiamethoxam and other neonicotinoid insecticide molecules do not produce steric hindrance when entering the channel. While the nicotine molecule cannot bind to the center of the protein channel, which proves that the nicotine molecule will produce steric hindrance when entering the channel.

The result above indicates that the BraPIP1;1 protein can transport neonicotinoid insecticides, but not nicotine.

EXAMPLE 5

Response of BraPIP1;1 Gene to Environmental Thiamethoxam Stress

Seedlings of Chinese cabbage with the same growth condition were put in a Hoagland's nutrient solution containing 10 mg/L thiamethoxam (the Hoagland's nutrient solution was purchased from Beijing Coolaber Technology Co., Ltd.), and treated in the Hoagland's nutrient solution for 6 and 24 hours (treatment group).

At the same time, a Hoagland's nutrient solution without thiamethoxam was used as the control group.

Treated root and aboveground tissue RNA of two groups was extracted respectively, the 1st strand cDNA was obtained by reverse transcription as a template, specific expression primers were designed based on the cDNA sequence of BraPIP1;1, the Chinese cabbage Tublin was used as an internal reference, and the expression of the gene transcription level was detected by quantitative RT-PCR.

Quantitative PCR primer design:

```
BraPIP1;1-F(SEQ ID NO. 5):
AACAGTACAGTGCCTTGA;

BraPIP1;1-R(SEQ ID NO. 6):
GACCTCCTTAGTGCTCAG;

Tublin-F(SEQ ID NO. 7):
ACTGGGTGTTTTGGGTTGGG;

Tublin-R(SEQ ID NO. 8):
TGAAGGGGATTGCTCTGATGAC.
```

The quantification instrument is 7500 Real Time PCR System (Applied Biosystem), and a qPCRT system was configured according to the instructions of a kit 2×TSINGKE Master qPCR Mix (Tsingke Biotechnology Co., Ltd.). The PCR program is: pre-denaturation at 95° C. for 10 min, at 95° C. for 15 s, and at 60° C. for 20 s, for 40 cycles.

Figure 4:
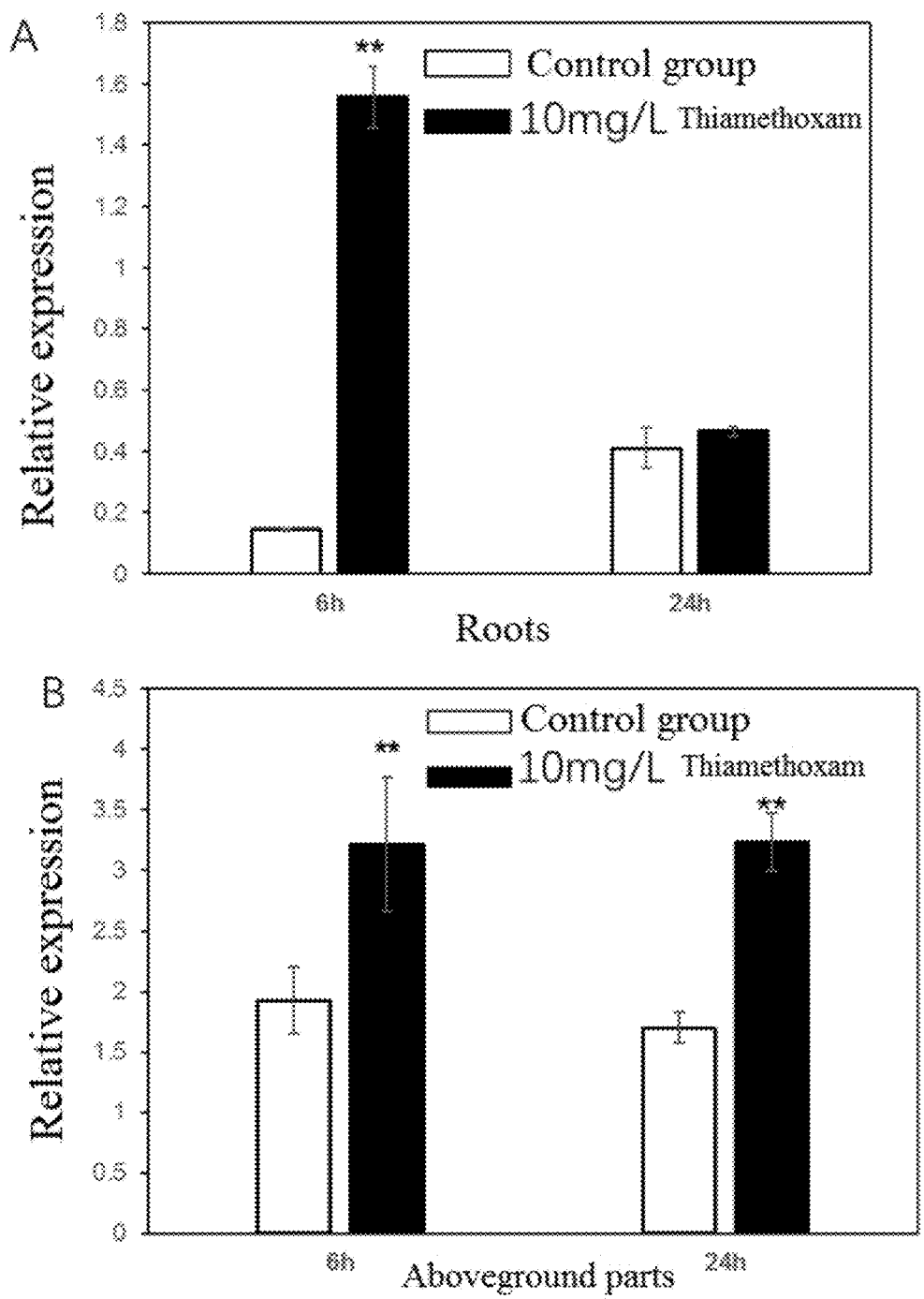

The result of qRT-PCR showed that BraPIP1;1 was expressed both in roots and aboveground parts. Compared with the control, under the condition of adding thiamethoxam, the expression abundance of BraPIP1;1 in the roots and aboveground parts was significantly increased after 6 hours of treatment ($p<0.001$), and after 24 hours of treatment, the expression abundance of the aboveground parts was significantly increased ($p<0.001$) (as shown in FIG. 4), indicating that the transport and utilization of thiamethoxam is related to the BraPIP1;1 aquaporin.

EXAMPLE 6

Overexpression of BraPIP1;1 Gene *Saccharomyces cerevisiae* Can Improve Stress Tolerance to Thiamethoxam The BraPIP1;1 gene cloned in Example 1 was constructed into the *Saccharomyces cerevisiae* overexpression vector pYES2 (purchased from Clotech) referring to (He Lin, Jiang Lili, Wang Yucheng, Analysis of the stress tolerance of Tamarix thioredoxin peroxidase (ThPrx1) gene transformed into yeast, Journal of Northeast Forestry University, 2011, Vol. 39. No. 4, 101-104), and the constructed recombinant plasmid was named pYES2-BraPIP1;1. The pYES2-BraPIP1;1 and an empty vector pYES2 were transformed into *Saccharomyces cerevisiae* INVSc1 by lithium acetate precipitation. The recombinant yeasts were named INVSc1 (pYES2-BraPIP1;1) and INVSc1 (pYES2), respectively.

Induction of recombinant strains: Single colonies of the control yeast INvsc1 (pYES2) and the recombinant yeast INvsc1 (pYES2-BraPIP1;1) were picked, inoculated in an SC-U liquid medium (with glucose of a final concentration of 2%) respectively, and incubated at 30° C. for 24 h on a shaker. The OD600 value is measured, and the amount of bacterial solution required is calculated such that the OD600 of bacteria in 10 ml of induction medium (SC-U+2% galactose) is 0.4. Induce expression was carried out at 30° C. for 24 h. The OD600 value was measured again, and the amount of bacterial solution required was calculated.

Growth experiment of the recombinant strains under thiamethoxam stress: Referring to the method disclosed in (He Lin, Jiang Lili, Wang Yucheng, Analysis of the stress tolerance of Tamarix thioredoxin peroxidase (ThPrx1) gene transformed into yeast, Journal of Northeast Forestry University, 2011, Vol. 39. No. 4, 101-104), the OD600 value of the induced bacterial solution is measured, and the amount of bacterial solution required is calculated such that the OD600 of bacteria in 200 μL of bacterial solution is 2. The bacterial solution was centrifuged at 8500 r/min for 1 min, and the supernatant was discarded.

Figure 5:
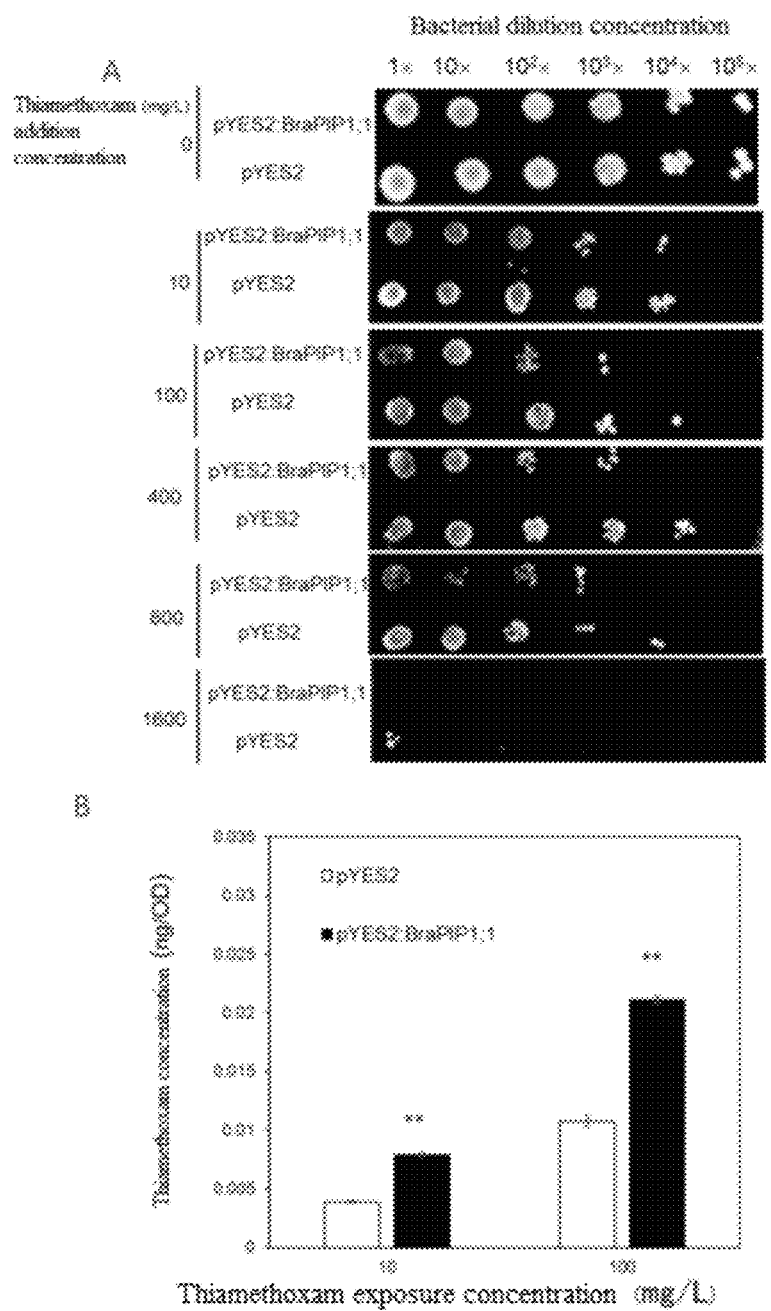

Thiamethoxam stress treatment: The bacteria were resuspended in 200 μL of thiamethoxam solutions of 0, 10, 100, 400, 800 and 1600 mg/L respectively, and subjected to stress at 30° C. for 72 h. The bacterial solutions were diluted by 10, 100, 1000, 10000 and 100000 times, and then 3 μL of bacterial solutions were spread on a solid medium of SC-U (with glucose of a final concentration of 2%), and incubated at 30° C. for 48 h. The result is as shown in FIG. 5A: The transgenic strain (pYES2-BraPIP1;1) grows the same as the wild strain (pYES2) without the thiamethoxam, and grows weaker than the wild strain with the thiamethoxam.

The thiamethoxam content experiment of the recombinant strains: The OD600 value of the induced bacterial solution was measured and the amount of bacterial solution required was calculated such that the OD600 of bacteria in 500 ml of bacterial solution is 0.1. The bacterial solution was centrifuged at 8500 r/min for 1 min, and the supernatant was discarded. The bacteria were resuspended in 500 ml of SC-U liquid media containing 10 and 100 mg/L thiamethoxam (with glucose of a final concentration of 2%) respectively, and subjected to stress at 30° C. for 6 h, and the OD600 value was determined. After centrifugation at 6000 rpm for 10 min, the bacteria were washed three times with ultrapure water, and disrupted with glass beads combined with ultrasound, and thiamethoxam was extracted to measure the amount. Under the stress of 10 mg/L thiamethoxam, the thiamethoxam content of the recombinant strain was 0.0078 ng/OD, which was significantly higher than that of the control strain (0.0038 ng/OD). Under the stress of 100 mg/L thiamethoxam, the thiamethoxam content of the recombinant strain (pYES2-BraPIP1;1) was 0.021 ng/OD, which was significantly higher than that of the control strain (pYES2, 0.011 ng/OD) (see FIG. 5B).

EXAMPLE 7

Overexpression of BraPIP1;1 Gene in *Arabidopsis thaliana* Can Increase the Uptake and Accumulation of Thiamethoxam in *Arabidopsis thaliana*

The BraPIP1;1 gene cloned in Example 1 was constructed into the plant binary overexpression vector pCAMBIA2301 (purchased from Clotech). By the *Agrobacterium tumefaciens*-mediated method (Valvekens, D., van Montagu, M., and Lijsebettens, M. V. (1988). *Agrobacterium tumefaciens*-mediated transformation of *Arabidopsis thaliana* root explants by using kanamycin selection. Proc. Natl. Acad. Sci. USA 85, 5536-5540.), the inflorescence of wild-type *Arabidopsis thaliana* Col-0 (purchased from ATCC, USA) was infected with the constructed overexpression vector. Through screening (resistance pure line seedlings were screened on a ½MS plate containing 50 μg/mL kanamycin), BraPIP1;1 overexpression *Arabidopsis thaliana* pure line materials BraPIP1;1#4 and BraPIP1;1#6 were identified and obtained.

Figure 6:
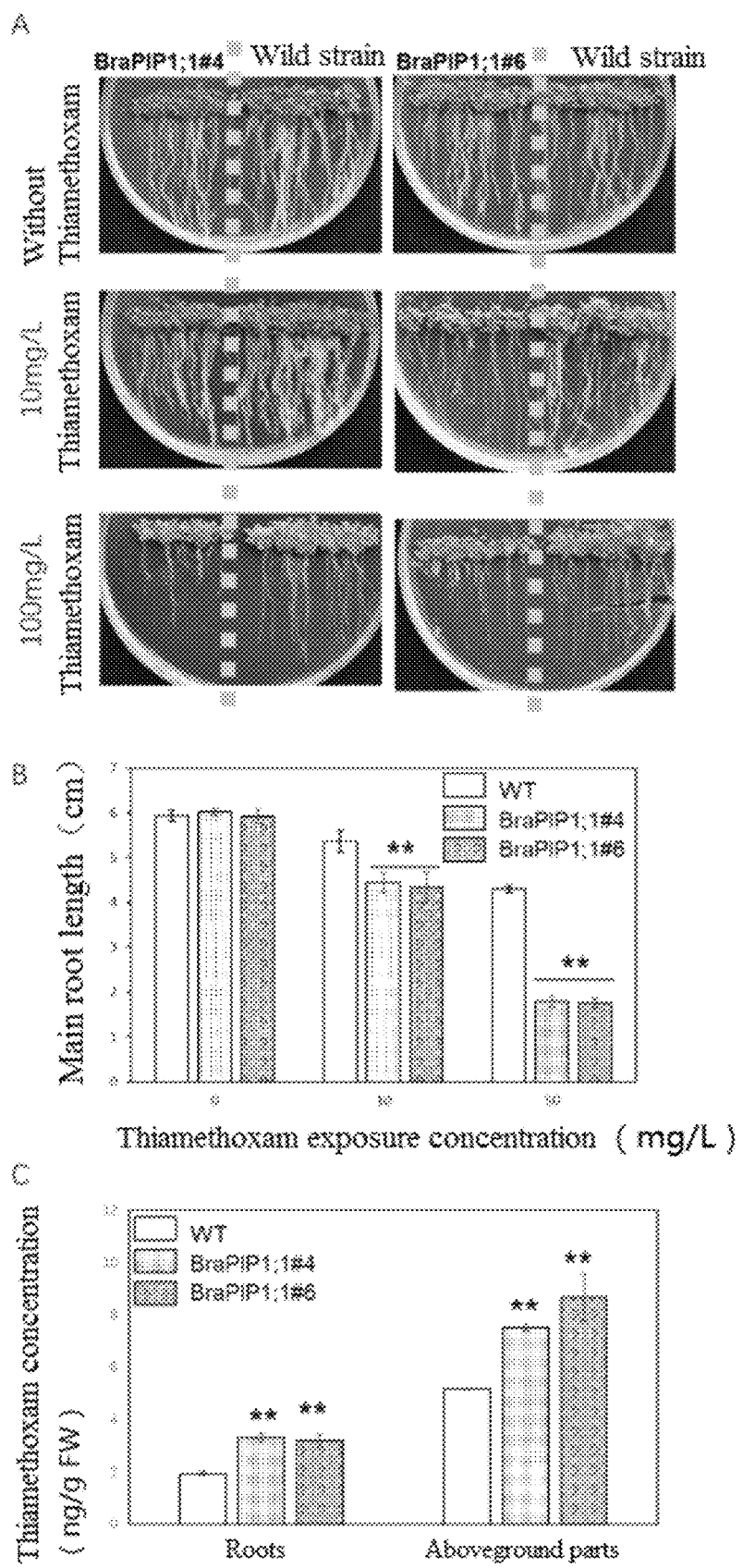

The pure line seeds of the BraPIP1;1#4 and BraPIP1;1#6 obtained in the previous transgenic experiment and a wild-type Col-0 material (WT) were germinated on a ½MS medium respectively, and then transferred to ½MS media (Qingdao Hopebio Co., Ltd., Item No. HB8469-12, PH=5.6) containing 10 and 50 mg/L thiamethoxam respectively. After 20 days, the growth of the seedlings was observed and the main root length was measured. The result is as shown in FIGS. 6A and 6B respectively. The main root length of the transgenic strain is shorter than that of the wild type.

In addition, germinated seedlings of the same size were transplanted into soil containing 10 mg/L thiamethoxam, and after 20 days of culture, the root and aboveground samples of the transgenic *Arabidopsis thaliana* and the control were harvested respectively, washed with deionized water, and weighed. The thiamethoxam content of each sample was measured and calculated with reference to (Wenfeng W, Wan Q, Li Y, et al. Uptake, translocation and subcellular distribution of pesticides in Chinese cabbage (*Brassica rapa* var. *chinensis*)[J]. Ecotoxicology and Environmental Safety, 2019.). The result is as shown in FIG. 6C. The thiamethoxam content of the roots and aboveground parts of the transgenic plant is higher than that of the wild plant.

The examples above illustrate that the aquaporin BraPIP1;1 gene resource has the characteristic of sensitively responding to neonicotinoid insecticides in the external environment. At the same time, it has the function of rapidly mediating the uptake and transport of neonicotinoid pesticides, promoting the accumulation of neonicotinoid pesticides in plants, which has important application value in improving (agricultural) crop utilization of pesticides and pesticide development, and lays a foundation for further improvement of pesticide structure and development of systemic pesticides to improve pesticide utilization.

The invention claimed is:

1. A method for uptake and transport of neonicotinoid insecticides by a plant, comprising:
   administering to the plant an amount of a plasma membrane intrinsic aquaporin having an amino acid sequence 100% identical to SEQ ID No. 2; and measuring a concentration of neonicotinoid insecticides in root and above ground portion of the plant, wherein the plant has an increased concentration of the neonicotinoid insecticides as compared to that of a control plant that does not comprise the administrated plasma membrane intrinsic aquaporin.

2. The method of claim 1, wherein the plants comprise at least one of vegetables, rice, *Zea mays*, wheat, rape and *Arabidopsis thaliana.*

3. The method of claim 1, wherein the neonicotinoid insecticides comprise at least one of thiamethoxam, imidacloprid, acetamiprid, nitenpyram and dinotefuran.

4. A method for promoting uptake and transport of neonicotinoid insecticides in a plant, comprising:

introducing a binary overexpression vector containing a nucleotide sequence 100% identical to SEQ ID No. 1 into the plant for expression; and measuring a concentration of neonicotinoid insecticides in root and above ground portion of the plant, wherein the plant has an increased concentration of the neonicotinoid insecticides as compared to that of a control plant that does not comprise the binary overexpression vector.

5. The method for promoting uptake and transport of neonicotinoid insecticides in plants of claim 4, wherein the plants comprise at least one of vegetables, rice, *Zea mays*, wheat, rape and *Arabidopsis thaliana.*

6. The method for promoting uptake and transportation of neonicotinoid insecticides in plants of claim 4, wherein the neonicotinoid insecticides comprise at least one of thiamethoxam, imidacloprid, acetamiprid, nitenpyram and dinotefuran.

7. The method of claim 1, wherein the increase in the neonicotinoid insecticides concentrations in root is 50% and in the above the ground portion is 50%-70%.

* * * * *

SEQUENCE LISTING

```
<160> NUMBER OF SEQ ID NOS: 8

<210> SEQ ID NO 1
<211> LENGTH: 861
<212> TYPE: DNA
<213> ORGANISM: Artificial Sequence
<220> FEATURE:
<223> OTHER INFORMATION: synthetic gene

<400> SEQUENCE: 1
atggaaggca aggaagaaga cgttagggtt ggagctaaca agttcccgga gagacaacca      60
ataggaactt cagctcagag cgacaaggac tacaacgagc caccaccagc gccgcttttc     120
gagcctggcg agctttcttc atggtccttc tggcgagctg gtatcgctga gtttatagct     180
actttcctct ttctctacat cactgttttg accgtcatgg gagttaaaag gtcaccgaac     240
atgtgttctt ccgtcggaat ccaaggtatc gcttgggcat tcggtggtat gatatttgct     300
cttgtctact gcaccgctgg tatctctggt ggacacatca acccagcggt cacttttggt     360
ctgttcttag cccggaagct gtcgcttacc agagctctgt actacatagt gatgcagtgc     420
ttgggagcca tatgcggagc tggtgtggtt aaagggttcc agcctaacca ataccaggct     480
ctaggaggag gagccaacac tgtggctcct ggatacacca aaggaagtgg tcttggagct     540
gagatcatcg gtactttcgt ccttgtttac acagtcttct cagccactga cgccaagaga     600
aacgcacgtg actctcatgt tcccattctt gcaccactcc caatcgggtt tgcggttttc     660
ttggttcact tagcaaccat cccaatcact ggcacaggca tcaacccggc tagaagtctt     720
ggagctgcaa tcatctacaa caaagaccat tcctgggacg accactgggt gttttgggtt     780
gggcccttca ttggtgctgc acttgctgct ctttaccatg tgattgtcat cagagcaatc     840
cccttcaagt ccagaaacta a                                              861
```

<210> SEQ ID NO 2
<211> LENGTH: 286
<212> TYPE: PRT
<213> ORGANISM: Artificial Sequence
<220> FEATURE:
<223> OTHER INFORMATION: from Chinese cabbage

<400> SEQUENCE: 2

Met Glu Gly Lys Glu Glu Asp Val Arg Val Gly Ala Asn Lys Phe Pro
1               5                   10                  15

Glu Arg Gln Pro Ile Gly Thr Ser Ala Gln Ser Asp Lys Asp Tyr Asn
            20                  25                  30

Glu Pro Pro Ala Pro Leu Phe Glu Pro Gly Glu Leu Ser Ser Trp
        35                  40                  45

Ser Phe Trp Arg Ala Gly Ile Ala Glu Phe Ile Ala Thr Phe Leu Phe
    50                  55                  60

Leu Tyr Ile Thr Val Leu Thr Val Met Gly Val Lys Arg Ser Pro Asn
65                  70                  75                  80

Met Cys Ser Ser Val Gly Ile Gln Gly Ile Ala Trp Ala Phe Gly Gly
                85                  90                  95

Met Ile Phe Ala Leu Val Tyr Cys Thr Ala Gly Ile Ser Gly Gly His
            100                 105                 110

Ile Asn Pro Ala Val Thr Phe Gly Leu Phe Leu Ala Arg Lys Leu Ser
        115                 120                 125

Leu Thr Arg Ala Leu Tyr Tyr Ile Val Met Gln Cys Leu Gly Ala Ile
    130                 135                 140

Cys Gly Ala Gly Val Val Lys Gly Phe Gln Pro Asn Gln Tyr Gln Ala
145                 150                 155                 160

Leu Gly Gly Gly Ala Asn Thr Val Ala Pro Gly Tyr Thr Lys Gly Ser
                165                 170                 175

Gly Leu Gly Ala Glu Ile Ile Gly Thr Phe Val Leu Val Tyr Thr Val
            180                 185                 190

Phe Ser Ala Thr Asp Ala Lys Arg Asn Ala Arg Asp Ser His Val Pro
        195                 200                 205

Ile Leu Ala Pro Leu Pro Ile Gly Phe Ala Val Phe Leu Val His Leu
    210                 215                 220

Ala Thr Ile Pro Ile Thr Gly Thr Gly Ile Asn Pro Ala Arg Ser Leu
225                 230                 235                 240

Gly Ala Ala Ile Ile Tyr Asn Lys Asp His Ser Trp Asp Asp His Trp
                245                 250                 255

Val Phe Trp Val Gly Pro Phe Ile Gly Ala Ala Leu Ala Ala Leu Tyr
            260                 265                 270

His Val Ile Val Ile Arg Ala Ile Pro Phe Lys Ser Arg Asn
        275                 280                 285

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
atggaaggca aggaagaaga cg                                          22

<210> SEQ ID NO 4
<211> LENGTH: 20

```
<212> TYPE: DNA
<213> ORGANISM: Artificial Sequence
<220> FEATURE:
<223> OTHER INFORMATION: primer

<400> SEQUENCE: 4
ttagtttctg gacttgaagg                                               20

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
aacagtacag tgccttga                                                 18

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
gacctcctta gtgctcag                                                 18

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
actgggtgtt ttgggttggg                                               20

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
tgaaggggat tgctctgatg ac                                            22
```